United States Patent
Clement et al.

(10) Patent No.: US 9,468,710 B2
(45) Date of Patent: Oct. 18, 2016

(54) VACUUM POWERED SALINE INJECTION SYSTEM

(71) Applicants: Thomas P. Clement, Bloomington, IN (US); S. Stone Linton, Bloomington, IN (US)

(72) Inventors: Thomas P. Clement, Bloomington, IN (US); S. Stone Linton, Bloomington, IN (US)

(*) Notice: Subject to any disclaimer, the term of this patent is extended or adjusted under 35 U.S.C. 154(b) by 0 days.

(21) Appl. No.: 14/086,434

(22) Filed: Nov. 21, 2013

(65) Prior Publication Data

US 2015/0141907 A1    May 21, 2015

(51) Int. Cl.
*A61M 1/00* (2006.01)
*A61M 3/02* (2006.01)
*A61B 18/14* (2006.01)

(52) U.S. Cl.
CPC ........ *A61M 1/0064* (2013.01); *A61B 18/1482* (2013.01); *A61B 2018/1422* (2013.01); *A61B 2018/1475* (2013.01); *A61B 2218/002* (2013.01); *A61B 2218/007* (2013.01); *A61M 1/00* (2013.01); *A61M 1/0056* (2013.01); *A61M 1/0068* (2014.02); *A61M 3/02* (2013.01); *A61M 3/0233* (2013.01); *A61M 3/0254* (2013.01); *A61M 3/0279* (2013.01); *A61M 3/0283* (2013.01); *A61M 2205/7545* (2013.01); *A61M 2205/7554* (2013.01)

(58) Field of Classification Search
CPC .. A61M 3/02; A61M 3/0254; A61M 3/0279; A61M 3/0233; A61M 1/00; A61M 1/0058; A61M 1/0062; A61M 1/0064; A61M 1/0066; A61M 1/0068; A61M 1/0074
See application file for complete search history.

(56) References Cited

U.S. PATENT DOCUMENTS

| | | | |
|---|---|---|---|
| 4,077,405 A * | 3/1978 | Haerten et al. | 604/66 |
| 4,315,506 A * | 2/1982 | Kayser | A61M 1/0037 251/63 |
| 4,997,420 A * | 3/1991 | LeFevre | 604/121 |
| 5,312,400 A * | 5/1994 | Bales et al. | 606/41 |
| 5,391,145 A | 2/1995 | Dorsey, III | |
| 7,000,267 B2 | 2/2006 | Chesters | |
| 7,959,597 B2 | 6/2011 | Baker | |
| 8,435,207 B2 | 5/2013 | Baker | |
| 2002/0017328 A1* | 2/2002 | Loo | 137/625.47 |
| 2005/0084395 A1* | 4/2005 | Kang | 417/392 |
| 2007/0112343 A1* | 5/2007 | Mische et al. | 606/41 |

* cited by examiner

*Primary Examiner* — Kami A Bosworth
*Assistant Examiner* — Nilay Shah
(74) *Attorney, Agent, or Firm* — Barnes & Thornburg LLP

(57) ABSTRACT

A method and apparatus for injecting saline into an open cavity of a patient's body, and, alternatively, vacuuming fluids from said cavity, during laparoscopic surgery that provides constant feed and amplified pressure to provide a steady fluid output, in a disposable, single use handheld surgical device.

3 Claims, 7 Drawing Sheets

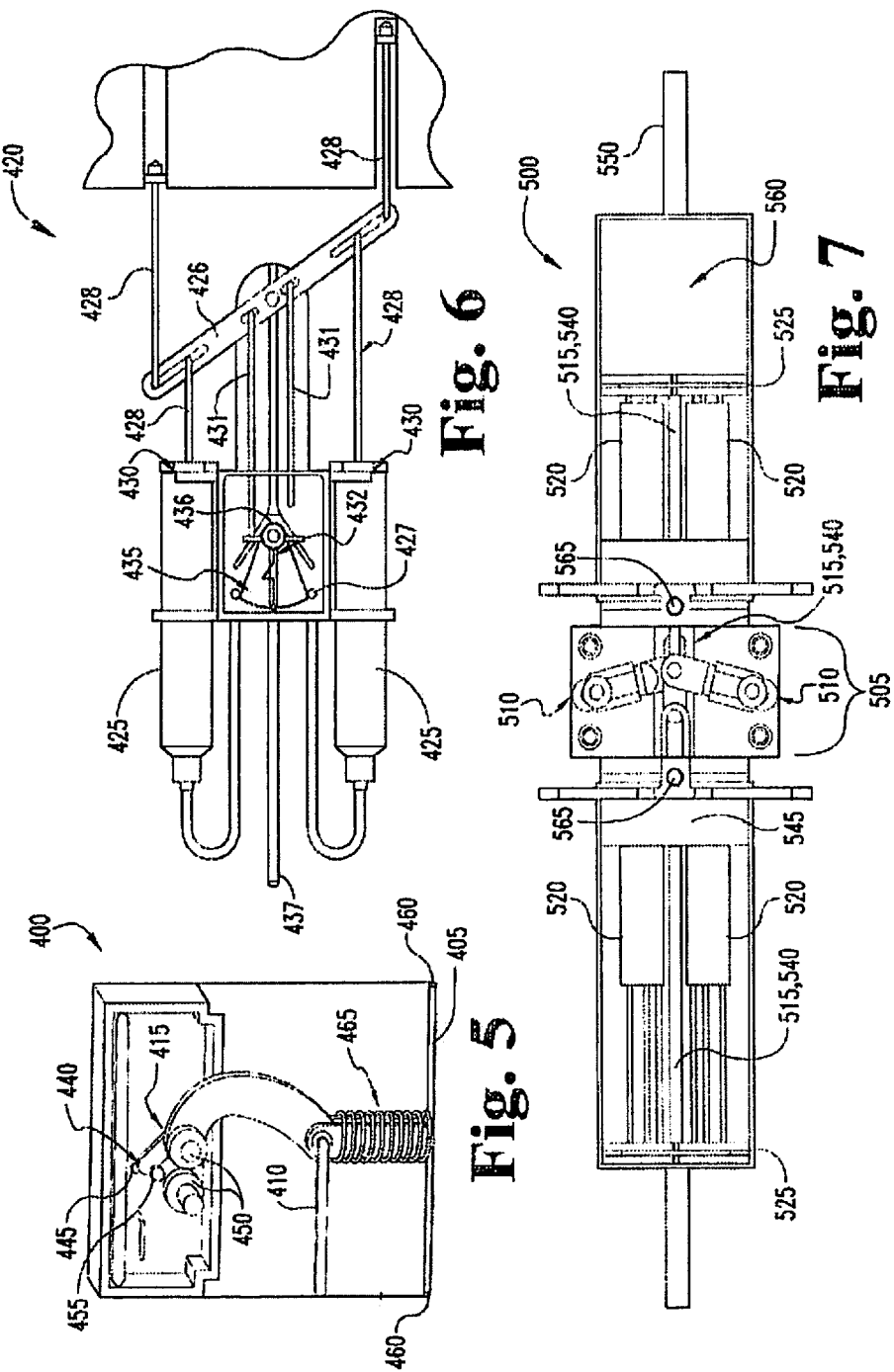

VACUUM POWERED SALINE INJECTION SYSTEM

TECHNICAL FIELD

The present novel technology relates to the field of medical device technology, and more particularly, a method and apparatus used during laparoscopic surgery for injecting saline into an open cavity of the patient's body, and, alternatively, vacuuming fluids from said cavity.

BACKGROUND

Laparoscopic surgery has continuously gained momentum and popularity since it was first introduced in the United States around 1988. Laparoscopic surgery, a minimally invasive surgical technique in which surgeons operate through multiple, small incisions in the abdomen, reduces standard risks, patient discomfort, scarring, and recovery time compared to previously utilized open surgical techniques.

Due to the intricate process of utilizing specialized instrumentation and a laparoscope camera to perform the operation while watching detailed images on a monitor, a clear surgical field is important. Without a clear surgical field, the surgeon is essentially operating "blind". Irrigation and aspiration are essential procedures during laparoscopic surgery, especially for maintaining a clear visual field and maintained hemostasis. Therefore, it is crucial that the device used for irrigation and aspiration provide enough hydraulic pressure to clear away debris, blood, blood clots, char, or any other material that may obstruct the surgeon's vision throughout the procedure, without delay.

Typically, disposable, single-use battery-powered laparoscopic devices are utilized for irrigation and aspiration. These mechanical pumping systems typically utilize standard alkaline batteries to power a motor, which in turn, activates a pump to drive irrigation fluid through the system for delivery to the operative site. Although these devices provide portable handheld systems with a built-in pump motor and generally adequate fluid pressure, there is currently a need for an aspiration and irrigation device that solves several issues unaddressed by the devices currently in the marketplace. The current solution is expensive and requires multiple disposal methods for proper disposal of the various components, such as metal, chemical, and surgical waste. In addition, an improved method of operating a pump, utilizing standard operating room resources, would be more transferable, efficient, inexpensive, and reliable. The present novel technology addresses this need.

BRIEF DESCRIPTION OF THE DRAWINGS

FIG. 5 is a front perspective view of a forth embodiment vacuum powered saline injection system.

FIG. 6 is a front perspective view of a fifth embodiment vacuum powered saline injection system.

FIG. 7 is a front perspective view of a front perspective view of a sixth embodiment vacuum powered saline injection system.

DESCRIPTION OF THE PREFERRED EMBODIMENTS

Figure 1:
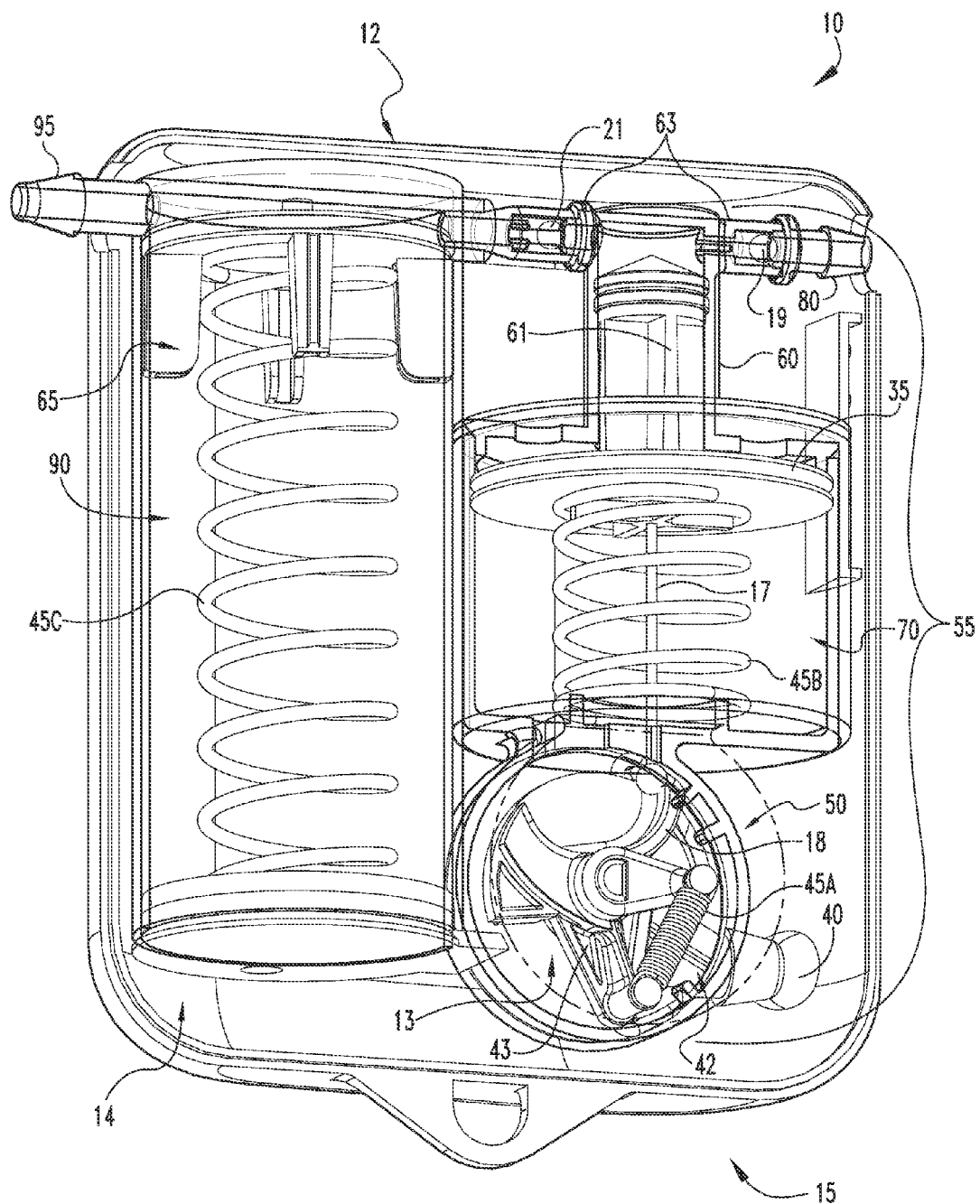
FIG. 1 is a front plan view of a vacuum powered saline injection system according to a first embodiment of the present novel technology.

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated device and such further applications of the principles of the novel technology as illustrated therein being contemplated as would normally occur to one skilled in the art to which the novel technology relates.

Figure 2:
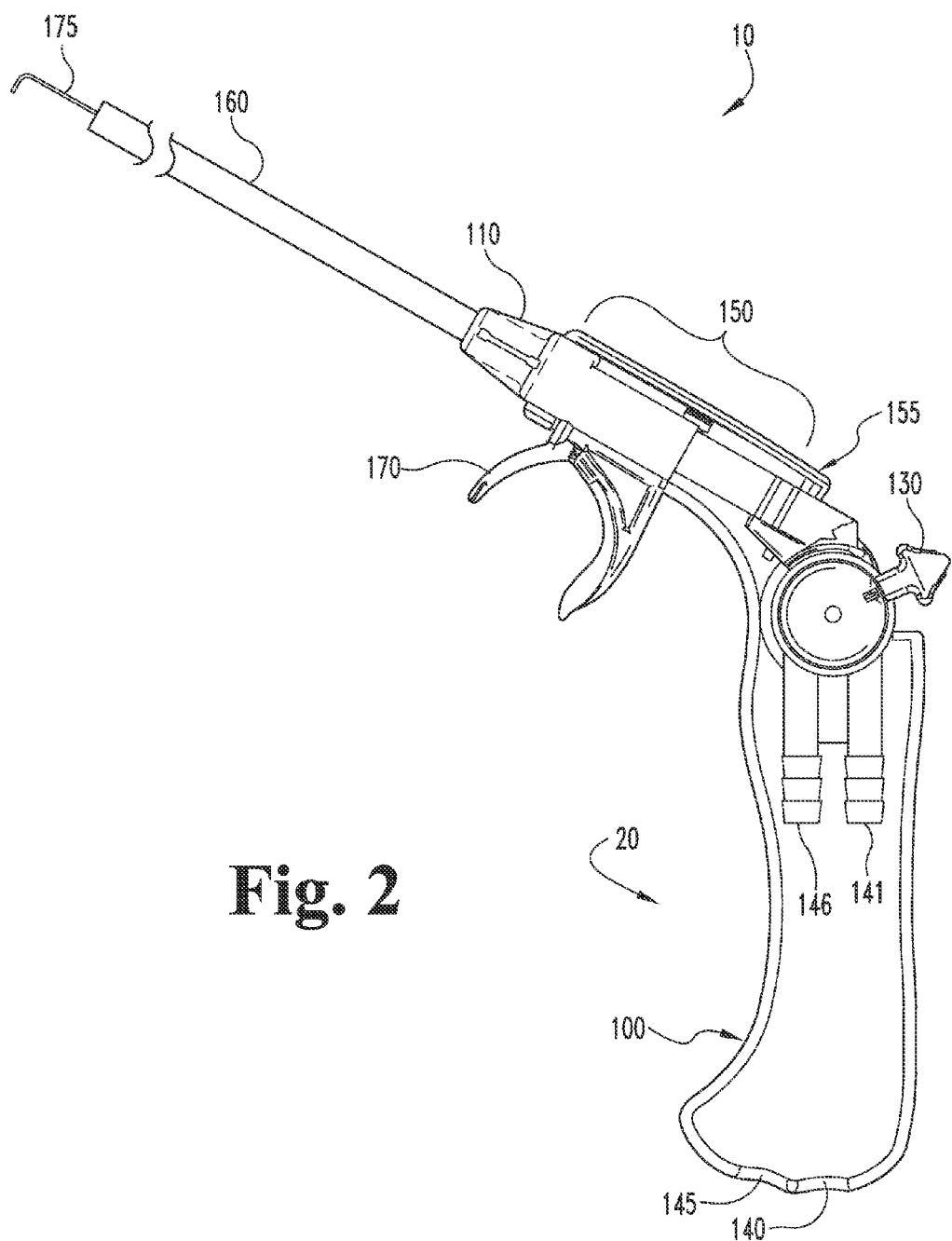
FIG. 2 is a side plan view of a first embodiment illustrating the gun portion of the vacuum powered saline injection system.
Figure 8:
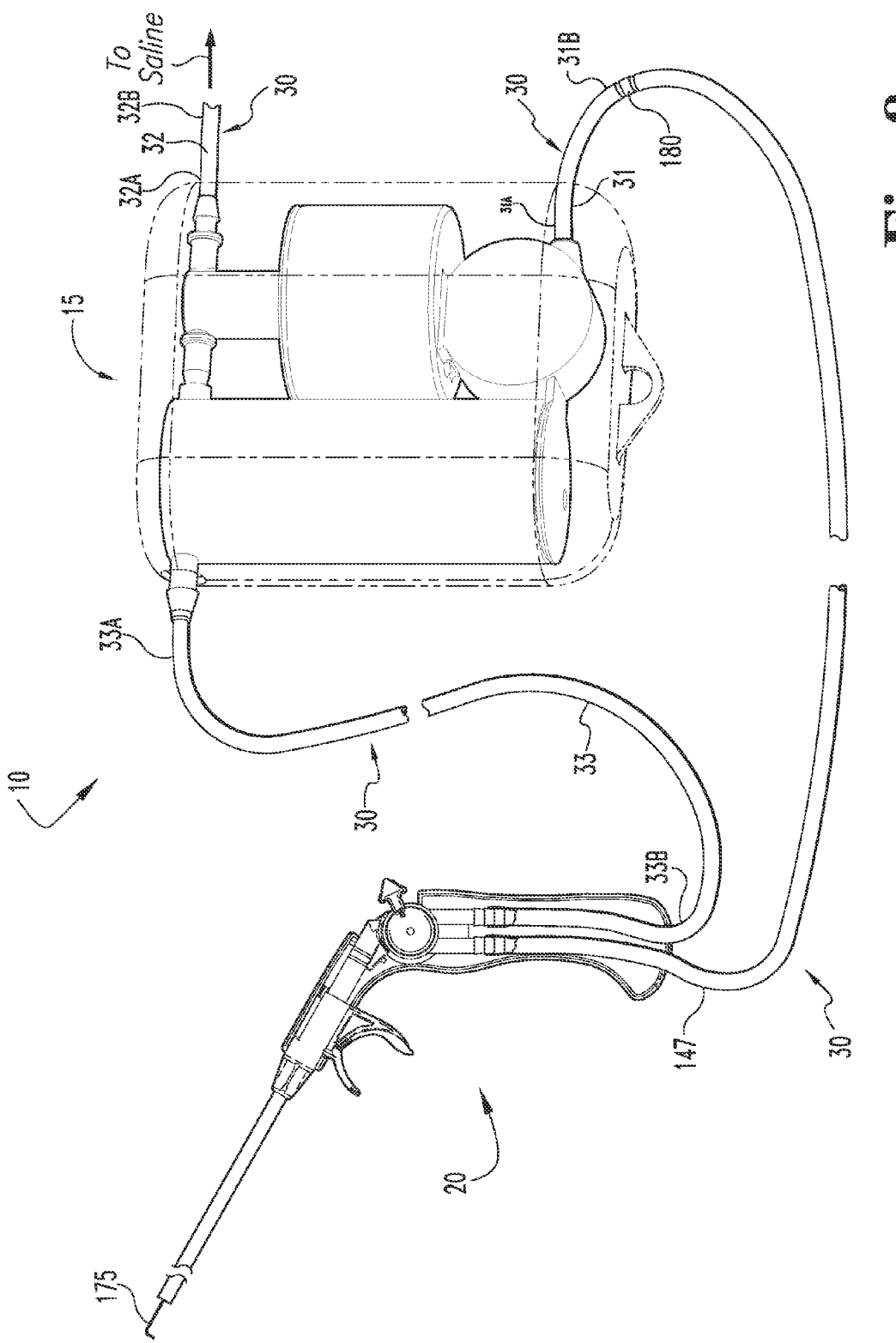
FIG. 8 is a front plan view of the first embodiment vacuum powered saline injection system illustrating both the pump portion and the gun portion.

FIGS. 1-2 and FIG. 8 illustrate a first embodiment of the present novel technology, a disposable, single-use handheld surgical vacuum powered saline injection system 10 for aspiration, and alternatively, irrigation during surgical procedures such as laparoscopic procedures. The vacuum powered saline injection system 10 generally includes a pump portion 15 and a wand or gun portion 20, and typically, a plurality of tubing portions 30, one of which operationally connects the pump 15 and gun portions 20 of the vacuum powered saline injection system 10.

The pump portion 15 generally includes a housing 12, which is customarily defined by a base portion 14 and an engageable cover portion (not illustrated in the drawings). Housing 12 is typically made of hard plastic or the like, although any convenient material may be selected. The housing 12 encases a pump motor 55, which typically includes a spring-biased valve 50 having a pivotable pump 13 connected in fluidic communication with a vacuum inlet 40, a generally cylindrical lower fluid storage chamber 70 (typically made of plastic or other polymeric material or the like) operationally connected to the spring-biased valve 50 and pivotable pump 13, a rod 17 extending vertically through the lower chamber 70 and down into the spring-biased valve 50 and pivotable pump 13, a generally cylindrical upper chamber 60 (typically made of plastic or other polymeric material or the like) in pneumatic communication with the lower chamber 70, a saline inlet 80 connected to the upper chamber 60, a generally cylindrical spring-biased accumulator or storage tank 90 (typically made of plastic or other polymeric material or the like) connected in fluidic communication to the upper chamber 60, and an outlet 95 for connecting the pump portion 15 and the gun portion 20 of the system 10 by way of a tubing component 33, in fluidic communication with the upper chamber 60 and flexible plastic tubing 30.

A vacuum source is connected in fluidic communication with inlet 40. The vacuum source is likewise connected to the lower chamber 70 through pivotable pump 13, such that when a partial vacuum is introduced, air pressure differentials are generated and air pressure urges disk member 35 against spring 45B, moving disk 35 toward pump 13, likewise pushing rod 17 into receptacle 18 and urging pivotable pump disk 13 to pivot in a first direction. Pivoting pump disk 13 generates a biasing force in spring 45A, which urges pivoting of disk 13 in a second, opposite direction. Disk 13 pivots in the first direction until port 43 is opened to atmosphere, allowing air into fluidic communication with vacuum source and disk member 35, reducing the pressure differential and enabling spring 45A to urge pivoting of disk 13 in the second, opposite direction and spring 45B to urge disk 35 away from disk 13. As disk 13 pivots in the second direction, port 43 is closed to atmosphere, air pressure in disk area 13 and around spring 45B under disk 35 decreases, and the pump circle repeats.

The side of disk 35 opposite spring 45B is connected to plunger 61 which is disposed inside upper cylinder 60. Movement of disk 35 towards disk 13 draws plunger 61 away from cylinder 60, generating a partial vacuum in cylinder 60 and urging fluid from saline source connected to inlet 80 through check valve 19 and into cylinder 60. As plunger 61 travels back into cylinder 60, saline therein is urged through check valve 21 into chamber/storage tank 90, urging disk 65 to move against spring 45C, compressing spring 45C and storing biasing energy therein. When outlet 95 is open, saline is urged from the tank 90. The vacuum pump motor 55 thus operates to fill tank 90 by urging saline thereinto with a first urging force. Once the tank is full, spring 45C and the incompressibility of saline generate a second, opposite force urging saline from outlet 95 when outlet is open and an unblocked fluid flow path exists; otherwise, the balance of forces prevent disk 35 from moving and the pump 55 automatically pauses.

The pump portion 15, gun portion 20, and plurality of tubing components 30, are powered by connection to a standard operating room medical vacuum system, allowing the vacuum powered saline injection system 10 to be utilized in most surgical and/or operating rooms. A first tubing component 31, has a proximal end 31A operationally connected to a fluid inlet port within the spring-biased valve 50 and pivotable pump 13, and a distal end 31B having a generally elastic, hydrocarbon polymer connector 180 operatively designed to engage a standard operating room medical vacuum system. In other embodiments, the connector 180 is sized and configured to engage non-standard vacuum sources, such as stand-alone vacuum pumps.

In operation, a flushing agent, such as isotonic saline, may be drawn from the distal end of a second tubing component 32, having a proximal end 32A operatively designed to engage a flushing agent from an outside source, and a distal end 32B in fluidic communication with the upper chamber 60 through a fluid inlet port 80. A generally T-shaped connector 63 made out of hard plastic, although any convenient material may be selected, is oriented within a first major axis, perpendicular to a generally small upper chamber 60 and in fluidic communication with both the upper chamber 60 and the spring-biased storage chamber 90, contains a plurality of typically round check valves, a first check valve 19 and a second check valve 21, to channel the incoming flushing agent between the upper chamber 60 and the spring-biased storage chamber 90. As the flushing agent enters the system 10 through the fluid inlet port 80, a first check valve 19 allows the flushing agent to enter the system 10 while a second check valve 21 blocks the flushing agent from passing through the generally T-shaped connector 63 to the spring-biased storage chamber 90. As the flushing agent enters the system 10, the spring-biased valve 50 and pivotable pump 13 operationally connected to a vacuum source, continuously cycle, urging a rod 17, generally connected to a first spring biased disk member 35 and typically extending vertically through the lower chamber 70 down into the spring-biased valve 50, to engage the spring 45C located within the spring-biased valve 50 to close a first port 43 operationally connected to an atmospheric opening. While a second port 42 operationally connected to a vacuum source is open, the first spring-biased disk member 35 is forced to draw against the biasing force and away from the upper chamber 60, producing a partial vacuum in the upper chamber 60, drawing the flushing agent into the upper chamber 60 and down into the lower chamber 70 as the spring-biased disk member 35 is compressed. As the pivotable pump 13 cycles, the spring-biased valve 50 forces a second port 42 operationally connected to a vacuum source to close, opening the first port 43 operationally connected to atmospheric air. The atmospheric air entering the system 10 negates the vacuum force entering the system, allowing the spring-bias 45 to urge a first spring-biased disk 35 positioned in the lower chamber 70, back towards the upper chamber 60, drawing the flushing agent back into the upper chamber 60. As the flushing agent is drawn back into the upper chamber 60 from the lower chamber 70, the first check valve 19 located within the generally T-shaped connector 63 moves towards the saline port 80 to block fluid from entering the vacuum powered saline injection system 10 from an outside source, forcing the flushing agent from the upper chamber 60 into the spring-biased storage chamber 90, containing a second spring-biased disk member 65. The method of forcing a flushing agent from the lower chamber 70 into a generally smaller upper chamber 60, while also forcing the flushing agent into the spring-biased storage tank 90 as the system 10 cycles, enables the system 10 to provide constant feed with amplified pressure, and thus, provide a constant, steady fluid output stream through a third tubing component, 33, having a proximal end 33A removably connected to the gun portion 20 of the system, and a distal end 33B in fluidic communication with the spring-biased storage chamber 90 through an inlet 95. The fluid output of the system 10 is controlled by the user through a multi-position valve 130 located on the gun portion 20 of the system, discussed in more detail herein. The vacuum powered pump further comprises an automatic shutoff feature when the spring-biased storage chamber 90 back pressure is equal to pump pressure forcing the fluid flow to cease through the system, the pivotable spring-biased pump 13 to stop pivoting, and the pump to idly wait until fluid is extracted from the storage chamber 90.

FIG. 2 generally illustrates the gun portion 20 of the vacuum powered saline injection system 10. The gun portion 20 (typically made of hard, electrically non-conducting plastic or the like, although any convenient material may be selected) is generally "L"-shaped, and is more typically ergonomically contoured for comfort and ease of use. The gun portion 20 typically contains a first inlet 140 for receiving a tubing component 33 to place the pump portion 15 in fluidic communication with the gun portion 20 through a tubing inlet 141 located within the pistol-shaped handle 100, and a second inlet 145 for receiving a vacuum tubing component 147, located on the underside of the pistol-shaped handle 100, through a second tubing inlet 146 located within the pistol-shaped handle 100, in fluidic communication to the storage chamber 90, as well as the operating room vacuum source. Additionally, a fluid nozzle 110 located on the barrel portion of the gun 150 places the handle 100 and barrel portions of the gun 150, including the vacuum tubing inlet 146, as well as the saline tubing inlet 141, in fluidic communication with the cannula 160. A multi-position valve 130, located on the top of the handle between the handle 100 and the barrel 150, permits a surgeon to quickly and easily manipulate whether the vacuum powered saline injection system 10 is in irrigation, aspiration, or off mode by simply rotating the typically circularly rounded valve 130 to the forward position, center, or back position. The multi-position valve 130 also permits a surgeon to control the flow and rate of a flushing agent, such as isotonic saline solution, or the rate and pressure of the vacuum. Thus, the gun portion's 20 functionality permits a surgeon to control aspiration or irrigation, as well as utilize a diathermy hook 175 located inside of a generally elongated cannula 160, without having to use additional tools, reach away from the operating table, and/or physically move to control the function of the system.

The generally hollow, cylinder-shaped cannula 160 houses a typically L-shaped spring-biased diathermy hook 175 that may be extended from the cannula 160 through an opening located on the distal end of the conduit 160. The diathermy hook 175 is typically made of surgical stainless steel or metal, although any convenient material may be selected, and is operationally connected to the moveable trigger 170 located on the barrel portion 150 of the gun handle 100. Actuation of the trigger 170 extends the hook from within the distal end of the cannula 160 in relative relation to the location of the trigger 170, to aid in clearing unwanted tissue beside linear structures during surgery.

Additional embodiments follow, wherein the vacuum powered saline injection system 10 operates as described above, however, the valve systems of the vacuum motor and the pump location differ. More specifically, the spring-biased valve 50 and the lower chamber 70 illustrated in FIG. 1 are replaced by alternative embodiments.

Figure 3:
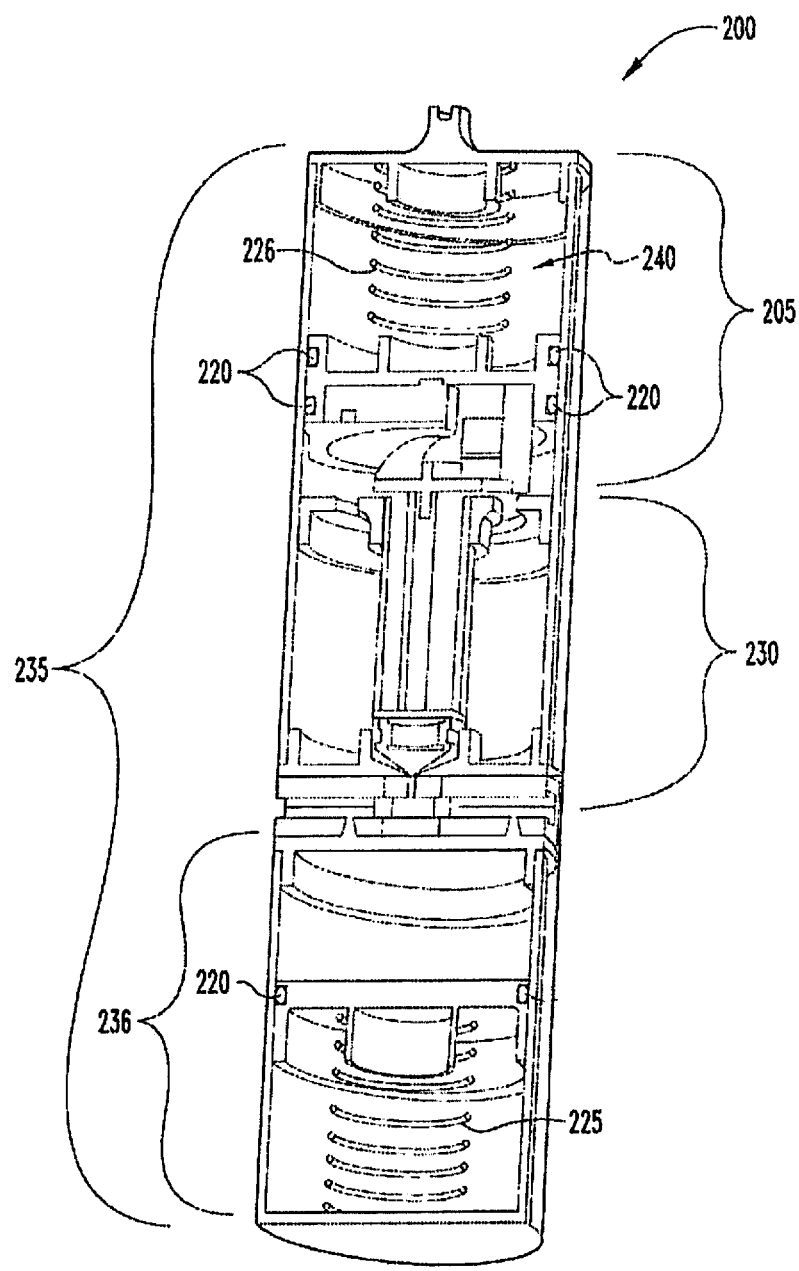
FIG. 3 is a front perspective view of a second embodiment vacuum powered saline injection system.

In an alternate embodiment, as illustrated in FIG. 3, a magnetically triggered valve system 200 cycles the saline pump assembly 235 by opening the vacuum chamber 240 to atmosphere when activated. Magnets (not shown), located on both the sliding valve gate (not shown) and the wall of the vacuum chamber 240, provide attractive and repulsive forces that allow the valve gate (not shown), located on the syringe pump 230, to move between alternating open and closed positions. In operation, the sliding gate valve (not shown) is initially in closed position sealing the vacuum chamber 240. As a vacuum is created within the vacuum motor 205, the atmospheric pressure pushes the syringe pump 230, compressing the spring bias 226 within the vacuum chamber 240 and the spring bias 225 within the accumulator 236, drawing a flushing agent such as saline into the attached spring bias syringe pump 230. As the syringe pump 230 passes the magnet (not shown) affixed to the vacuum chamber wall, the magnet embedded in the sliding valve gate (not shown) is repelled, allowing atmosphere to equalize in the vacuum chamber 240. The energy stored in the vacuum chamber 240 spring bias 226 pushes the syringe pump 230, discharging the saline. As the syringe pump 230 returns to the home position with the sliding valve gate (not shown) in closed position, the magnet in the sliding valve gate is attracted to the chamber mounted wall magnet, sealing the vacuum chamber 240 and concluding the stroke cycle.

Figure 4:
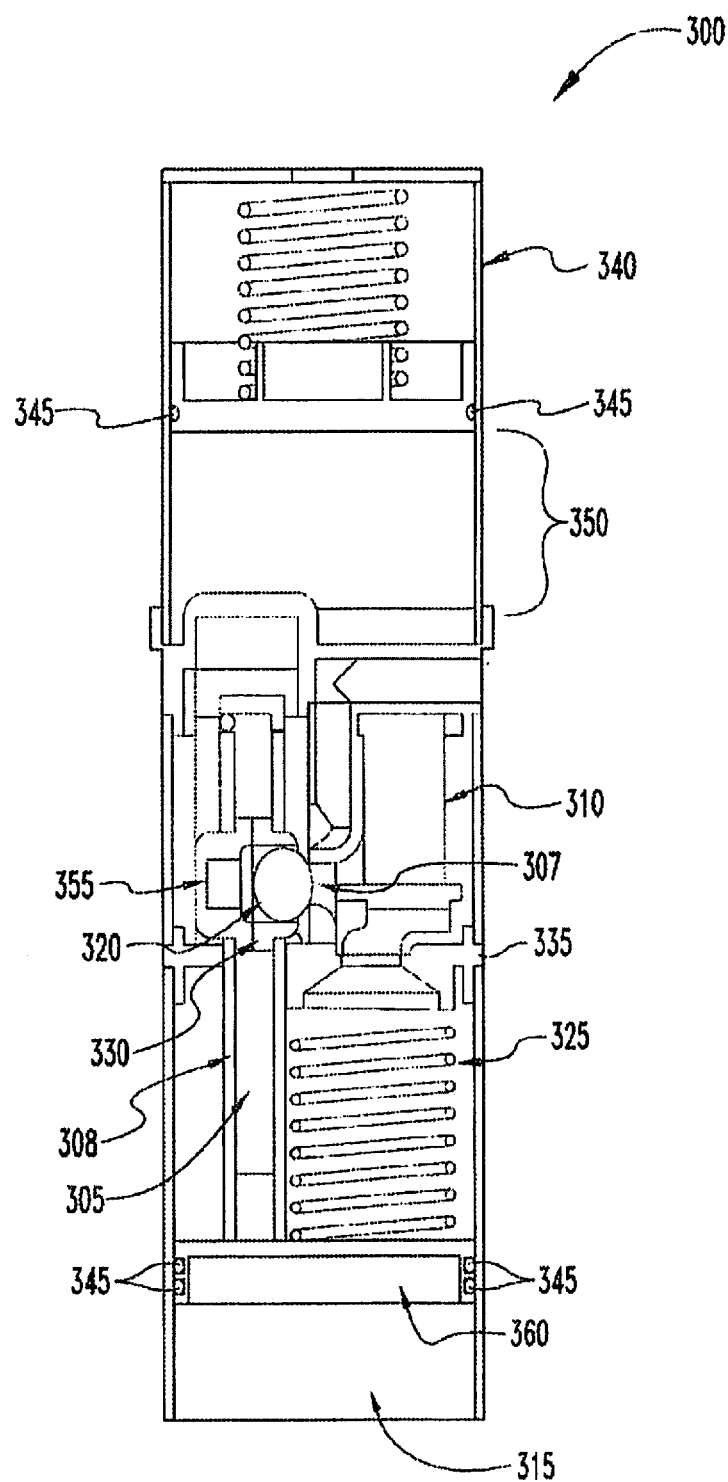
FIG. 4 is a front perspective view of a third embodiment vacuum powered saline injection system.

In another alternate embodiment, as illustrated in FIG. 4, a roller ball valve system 300 contains a lifter 305 that is operationally attached to the motor plunger 360 within the vacuum chamber 315 that actuates a spring-loaded roller ball 320 that opens and closes the atmospheric inlet 307 allowing atmosphere into the vacuum chamber 315. While engaging a vacuum source, vacuum is applied to the vacuum chamber 315 and atmosphere pushes the motor plunger (not shown) and check valve 310 which drives the lifter 305 and compresses the motor spring 325. The spring-loaded roller ball 320, located in a slotted track 308 of the lifter 305 containing an independent spring-loaded push-rod 330, compresses forcing the roller ball valve 355 to open the vacuum chamber 315 to atmosphere and close the vacuum supply port 335. Thereafter, the motor spring 325 releases, pushing the motor plunger (not shown) and attached saline chamber accumulator 350 to discharge saline through the attached syringe pump 340 and return to home position wherein the slot on the lifter [13081] 305 returns the roller ball assembly 320 to home position, sealing the vacuum chamber 315 and opening the vacuum supply port 335. A plurality of O-Rings 345 located between the vacuum chamber 315 and vacuum motor plunger 360, as well as between the saline chamber accumulator 350 and the pump 340, provides a fluid-tight seal when required.

In another embodiment, as illustrated in FIG. 5, the vacuum powered saline injection system 10 valve contains an over-the-center toggle system 400 wherein the pump is driven by the linear motion of the motor plunger 405, wherein O-rings 460 are located thereon. A motor plunger 405 directly attached to a push-rod lifter 410 located within the vacuum chamber alternatively forces the atmospheric port 445 or the vacuum port 455 to open, and alternately close when the over-the-center spring 450 loaded toggle 415 assembly strikes a valve or gate valve 440 that is spring 465 driven.

In an additional embodiment, as illustrated in FIG. 6, an alternate over-the-center toggle valve system 400 contains an adjacent vacuum redirect valve system 420 wherein the vacuum, entering the system 10 through a vacuum supply line 437 into vacuum ports 427 is redirected to alternating vacuum chambers 425. Each chamber 425 has a plunger 430 operationally connected to a connecting lever 426 via a plunger push-rod 428 extending from both sides of the connecting lever 426 to the saline pump. The connecting lever 426 drives a second set of push-rods 431 for the over-the-center toggle 432 via a spring bias 436, to redirect vacuum flow and the pump.

In an additional embodiment, as illustrated in FIG. 7, the vacuum powered saline injection system 10 contains a vacuum connection 550 to an inline vacuum redirect valve 500 wherein the over-the-center toggle valve system 505 is comprised of spring loaded levers 510 driven by a central slotted push-rod 515/540 connected to two vacuum chambers 560. Atmosphere alternately pushes the motor plungers 525 through the use of check valves 565 located between the over-the-center toggle valve center and the saline pump 545 and saline pump syringes 520, driving the central push-rod 515/540 and pumps. As the slotted central push-rod 515/540 moves the redirect valve that is held in place by spring loaded levers 510, the vacuum is applied to each vacuum chamber 560 sequentially. The saline pump syringes 520 are positioned in line with the shown vacuum chambers 560 and are attached to the spring loaded levers 510 by push-rods 540.

Figure 9:
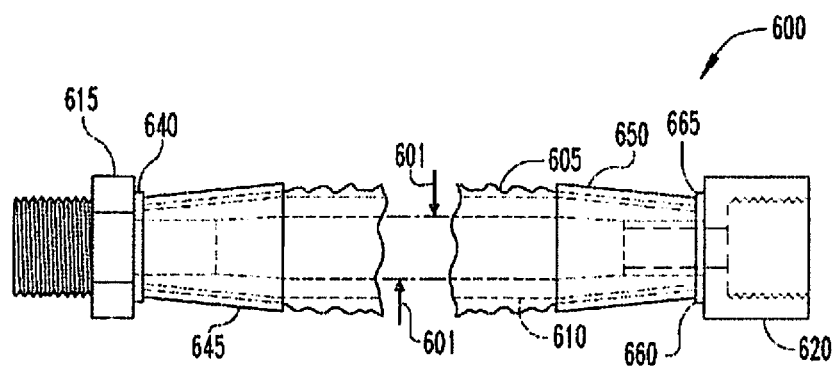
FIG. 9 is a side plan view of a seventh embodiment illustrating the accumulator portion of a vacuum powered saline injection system in its contracted state.
Figure 10:
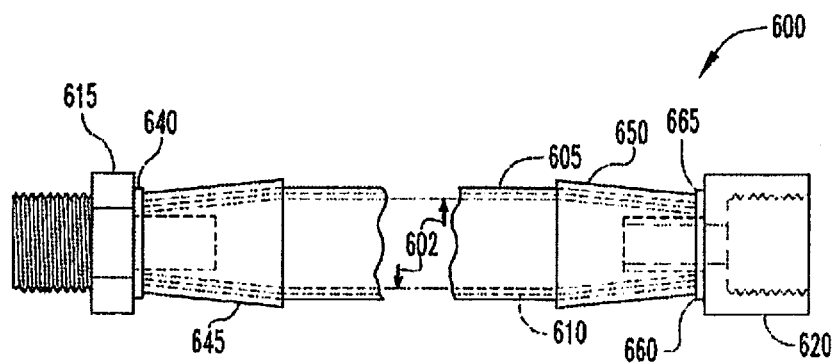
FIG. 10 is a side plan view of the seventh embodiment illustrating the accumulator portion of a vacuum powered saline injection system in its expanded state.

In an alternative embodiment, as illustrated in FIGS. 9 and 10, the system 10 functions as described above regarding the first embodiment 10, with the exception being that the accumulator 90 has been replaced by an expanding length of hose/tubing 600. The tubing 600 is typically self-expanding 602 upon application of fluid pressure and increased fluid volume causing a restricting force within the hose 600 and, more typically, self-contracting 601 upon release of the fluid pressure and fluid volume from within the hose 600. The hose 600 is typically composed of two separate and distinct tubes—an inner tube 605 and an outer tube 610, both at least partially encased within an expansion restrictor sleeves 645, 650. The inner tube 605 is typically formed from a material that is elastic and has the ability to expand from its relaxed or unexpanded length when a pressurized fluid is introduced into the elastic inner tube 605 and expands radially outwardly or laterally, with respect to its length; the radial expansion of the inner tube 605 is constrained by the maximum diameter of the non-elastic outer tube 610. The outer tube 610 is typically formed from a relatively non-elastic, relatively soft, bendable, tubular webbing or like material that is typically strong enough to withstand internal pressures of up to 250 pounds per square inch, (psi).

The hose 600, in its contracted form 601 as illustrated in FIG. 9, results from a lack of force being applied to the inner tube 605, allowing a flushing agent to enter the storage tank or accumulator 90. The fluid pressure within the hose 600 is generated by introducing fluid under pressure into one end of the hose 600 and restricting the flow of the fluid out of the other end of the hose 600, typically controlling fluid passage through the use of washers 660 located on a male coupler 615 and a female coupler 620, positioned on opposite ends of the flexible tubing 600. As a pressurized fluid is introduced into the elastic inner tube 605 in its contracted and relaxed state 601, the elastic inner tube 605 begins to expand laterally and longitudinally and the outer tube 610 begins to unfold and uncompress around the circumference of the elastic inner tube 605. Consequently, when the inner tube 605 expands to a predetermined degree, the outer tube 610 unfolds, and uncompresses along the entire length of the inner tube 605 until it reaches the same length as the inner tube 605 in the expanded condition 602. Also, because the inner tube 605 expands both longitudinally and laterally and its expansion is constrained by the non-elastic outer tube 610, the inner tube 605 fills all of the available space inside the non-elastic outer tube 610 and thus the surface of the unfolded, uncompressed outer tube 601 becomes smooth in the expanded condition 602 (as depicted in FIG. 10), generating an urging force upon the stored fluid within the accumulator 90 for discharge of saline from the system 10, when the valve 50 is open.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

What is claimed is:

1. A system for injecting and removing fluids during electro surgery:
   comprising:
      a pump portion;
      a fluid storage chamber operationally connected to the pump portion; and
      a wand portion connected in fluidic communication with the pump portion;
      wherein when the pump portion is fluidically connected to a vacuum source and fluidically connected to a fluid reservoir, a vacuum pump operable to urge fluid from the reservoir and into the fluid storage chamber with a first urging force;
      wherein fluid filling the storage chamber works against an energy storage member to generate an opposite biasing force;
      wherein the pump portion further comprises: a vacuum powered pump motor;
      a vent port in communication with an atmospheric pressure;
      a hose operationally connected to the vacuum powered pump motor for connection to the vacuum source;
      a spring-biased valve operationally connected to the hose; an operationally connected cylindrical vacuum chamber; a spring-biased disk positioned within the cylindrical vacuum chamber and operationally connected to the spring-biased valve;
      a fluid pumping chamber; a fluid pumping plunger operationally connected to the spring-biased disk; a fluidic inlet port operationally connected to the fluid pumping chamber and connectable in fluidic communication with the fluid reservoir;
      a fluidic outlet port operationally connected to the fluid storage chamber; a first check valve operationally connected between the inlet port and the pumping chamber; and
      a second check valve operationally connected between the outlet port and the fluid storage chamber;
      wherein when the pump portion is connected to the vacuum source and to the fluid reservoir, the spring-biased disk moves with the atmospheric pressure creating a reciprocating action alternately rotating the spring-biased valve to open and close the vent port; and
      wherein when the spring-biased disk connected to the fluid pumping plunger moves with the atmospheric pressure, a biasing force is generated to urge the fluid from the fluid reservoir to the fluid storage chamber.

2. The system of claim 1 wherein the wand portion further comprises a hook extending through a cannula and a trigger operationally connected to the hook, wherein actuation of the trigger extends the hook from within the cannula.

3. The system of claim 1 wherein the fluid storage chamber is an at least partially elastic flexible hose.

* * * * *